United States Patent [19]

Cercone et al.

[11] Patent Number: 5,556,391
[45] Date of Patent: Sep. 17, 1996

[54] SURGICAL SPONGE DEVICE

[75] Inventors: Ronald J. Cercone, East Lyme; Dom L. Gatto, Branford; Arthur A. Gertzman, Woodbridge; Douglas R. Valentine, Oakdale, all of Conn.

[73] Assignee: Merocel Corporation, Mystic, Conn.

[21] Appl. No.: 130,433

[22] Filed: Oct. 1, 1993

[51] Int. Cl.⁶ .............................. A61F 13/15; A61F 13/20
[52] U.S. Cl. ........................ 604/369; 604/378; 604/304; 602/46
[58] Field of Search ........................... 602/41–43, 46–47, 602/51, 58–59; 604/304, 358, 365–367, 369–370, 378, 385.1

[56]  References Cited

U.S. PATENT DOCUMENTS

| | | |
|---|---|---|
| 1,754,806 | 4/1930 | Stevenson . |
| 3,157,178 | 11/1964 | Bentov ..................................... 602/46 |
| 3,648,692 | 3/1972 | Wheeler . |
| 3,900,027 | 8/1975 | Keedwell . |
| 3,934,587 | 1/1976 | Gordon . |
| 4,054,141 | 10/1977 | Schwaiger et al. . |
| 4,292,972 | 10/1981 | Pawelchak et al. . |
| 4,381,611 | 5/1983 | Wishman . |
| 4,428,720 | 1/1984 | Van Erden et al. . |
| 4,502,156 | 3/1985 | Wishman . |
| 4,540,414 | 9/1985 | Wishman . |
| 4,550,725 | 11/1985 | Wishman . |
| 4,660,553 | 4/1987 | Naylor et al. ............................. 602/46 |
| 4,664,662 | 5/1987 | Webster .................................... 604/369 |
| 4,925,453 | 5/1990 | Kannankeril . |
| 4,961,735 | 10/1990 | Siciliano . |
| 4,967,758 | 11/1990 | Masciarotte . |
| 4,997,425 | 3/1991 | Shioya et al. . |
| 5,009,652 | 4/1991 | Morgan et al. . |
| 5,019,064 | 5/1991 | Eilender . |
| 5,078,709 | 1/1992 | Siciliano . |
| 5,098,775 | 3/1992 | Harada et al. . |
| 5,336,163 | 8/1994 | Demane et al. ......................... 602/46 |
| 5,447,505 | 9/1995 | Valentine et al. ....................... 604/304 |

FOREIGN PATENT DOCUMENTS 265906  5/1988  European Pat. Off. .............. 604/304

OTHER PUBLICATIONS

*Synthetic Substitutes for Skin,* Chardack et al., Plastic In Reconstruction Surgery, vol. 30, No. 5, (Nov. 1962).

Primary Examiner—Randall L. Green
Assistant Examiner—P. Zuttarelli
Attorney, Agent, or Firm—Gipple & Hale; John S. Hale

[57] ABSTRACT

A surgical device constructed of a polyvinyl acetal having a body constructed with an average pore diameter ranging from about 0.02 to about 1.2 mm and a fused surface layer of about 0.25 min. The fused surface layer is substantially closed and has a pore diameter ranging from about 0.01 to about 0.45 mm allowing absorption of fluid into the body of the device.

14 Claims, 2 Drawing Sheets

SURGICAL SPONGE DEVICE

BACKGROUND OF THE INVENTION

1. Field of Invention

The present invention generally relates to sponge surface treatments and more specifically is directed towards a sterile cellular synthetic sponge device made of polyvinyl acetal which has had its surface treated to form a substantially closed surface, retarding tissue ingrowth and also providing a surface layer with reduced wicking.

2. Description of the Prior Art

The literature is replete with references to various types of foam materials including polyurethane, polyisocyanate, polystyrene, polyolefin, polyvinyl chloride, epoxy, urea-formaldehyde, latex, silicone, and fluoropolymer and with methods of controlling the foam or sponge density and other bulk properties during manufacture.

Advances in the development of synthetic polymers have produced radical changes in wound care dressings, bandages, and medical sponges. Factors such as water vapor, oxygen permeability, bacterial impermeability, and selective absorption can be incorporated into new formulations. These new formulations also address specific requirements such as conformability, non-adherence, and adhesiveness. Thus, a family of polymeric products has been formed for wound care including polymeric foams, polymeric films, particulate and fibrous polymers, hydrogels and hydrocolloids.

The optimum wound handling characteristics for wound care dressings and bandages are expressed in general terms such as a) removal of excess exudate and toxic components; b) maintaining a high humidity or moistness at the wound/dressing interface; c) allow gaseous exchange; d) providing thermal insulation; e) protecting against secondary infection; f) freeing the wound from particulate contaminants; and g) removal of the dressing from patient without pain or trauma. Even with the advances in technology, it should be noted that there is no simple dressing or device that can produce the optimum micro environment for all wounds or for all the healing stages of a single wound.

Common factors that impair wound healing include the following:

a). Necrosis, slough and eschar; b) Prolonged inflammation; c) Hypoxemia; d) Vascular insufficiency; e) Protein malnutrition; f) Infection; g) Steriod medications; h) Dehydrated wound bed; and i) Anemia. "How do you score?: Test your skills in Pressure Ulcer Management", p. 197, Joan E. Halpin-Landry, *Chronic Wound Care,* ©1990.

Sponges and other packing materials used for nasal, sinus or otic packing require a high degree of absorptivity. They normally will swell as body fluids are absorbed. However, current materials and sponges such as porous foams support the coagulated blood and proteins exuding from the cavity surfaces that have been disrupted by surgery or trauma. These coagulated materials enter the pores of the sponge and dry in place. When it is necessary to remove these sponges, they stick to the tissue surface causing pain and occasionally rebleeding.

Thus, there exists the need for a sponge dressing or medical sponge device which has a surface which prevents tissue ingrowth while maintaining the favorable property of absorbing exudate or fluid from the wound area or patient cavity. Another need for such a sponge is that the sponge can swell to provide pressure against the disrupted tissue surface without sticking. Another problem that occurs with a dressing or other medical device inserted in the human body is the mechanical debridement of the wound or cavity caused by firm adhesion of the dressing or device to the wound or cavity because of tissue ingrowth. This adhesion is caused by fibrin produced by the wound or cavity and subsequent spreading of fibroblasts and capillaries.

U.S. Pat. No. 4,997,425 discloses using a porous wound dressing including a first sponge layer for contacting a wound and a second surface remote from a wound. The second surface, the surface remote from the wound, has a pore size smaller than the first surface.

The U.S. Pat. No. 4,054,141 describes a molded absorptive body including an absorptive layer of hydrophilic fibers and a sheath of the hydrophilic fibers bound together by thermoplastic particles. The absorptive body may be provided with a sheath on all sides or only on part of the body. See also U.S. Pat. Nos. 4,381,611; 4,502,156; 4,540,414 and 4,550,725 which show a nonwoven polypropylene fabric in the form of staple or continuous filaments which have been drawn and needled to form a web or batt which is fused on one side. When the fabric is wetted, water is released through the fused side but is not released through the unfused side. Conversely, when the fabric is wetted, the moisture adsorbed on the unfused side migrates or wicks through the fabric toward the fused side. When used as a bandage, the unfused side is in contact with the skin of the wearer.

The U.S. Pat. No. 3,934,587 discloses a solid sheet or film of a polymeric compound containing chemically reactable hydroxyl or amine groups that is reacted in a vapor phase mixture of acid chloride and aldehyde to form a product which is water-repellent on the treated side but water-permeable on the opposite, untreated side. The reactant sheet may be constructed of polyvinyl alcohol.

In addition to the aforenoted references, topical dressings for burn protection used in absorbing necrotic tissues and exudate are shown by U.S. Pat. No. 3,648,692. The dressing of this patent has a thin wound facing layer of dressing constructed of any of a number of various neutral synthetic reticulated open-cell solid foam or sponge materials covered with a barrier membrane. The thickness of the sponge facing layer is noted as being critical (preferably about one-sixteenth of an inch) for positioning of the barrier so that debris, fluids, etc. contained therein are accessible for phagocytic invasion from the body surface. If the layer is too thick, it is noted that segregated exudate located at the interface is not reached by the natural phagocytic action with the undesirable result that infection takes place and spreads within the dressing thereby delaying or preventing the healing process. Another foam sponge product constructed of lyophilized hydrocolloid foam which is capable of absorbing body exudates is shown in U.S. Pat. No. 4,292,972. The wound dressing is preferably constructed of a thin outer oxygen and vapor-permeable film and a layer of an absorbent adhesive such as hydrogel for adhering the wound dressing to the skin and for acting as a reservoir for wound exudate absorbed therein. A layer of collagen, in the form of a sponge or film is adapted for placement directly on the wound, the collagen layer being of smaller dimensions than the absorbent adhesive layer so that areas of the adhesive layer extending beyond the periphery of the collagen layer can be applied to the skin surrounding the wound to adhere the dressing in place.

U.S. Pat. No. 5,009,652 discloses a disposable laminated medical sponge or wipe which has a thin sheet that is impermeable to infectious agents as well as non-wettable by water and a layer of absorbent material having an area which is smaller than that of the impermeable sheet, laminated to the impermeable sheet. The peripheral edges of the absorbent layer are spaced inwardly from the peripheral edges of the impermeable sheet providing a surrounding rim that consists of the impermeable sheet so that liquid which contacts the layer of absorbent material cannot travel through and over the peripheral edge of the impermeable sheet to reach the opposite side of the impermeable sheet.

U.S. Pat. No. 4,967,758 discloses a three layer disposable liner for use with sphygmomanometers. The first layer of the liner is a non-woven web which allows moisture to pass through to a second or middle layer of absorbent material which collects and holds moisture with the third layer being of a thin vapor proof plastic.

U.S. Pat. No. 4,925,453 discloses a medical sponge for use as a wipe to absorb body fluids such as blood which protects the person using the sponge from contact. The sponge is constructed with an absorbent pad covered on one face by a fluid permeable cover sheet and on the other face by a fluid impervious cover sheet, both of the cover sheets enclosing the absorbent pad.

U.S. Pat. No. 4,961,735 discloses a method of using an evaporating bandage which drains body fluids from surgical incisions, wounds and burns. The bandage is constructed with two staggered layers of different woven material. The first layer is made of an absorbent material and the second layer is made of a non-absorbent material.

U.S. Pat. No. 3,900,027 shows a process for making integral absorbent pad bandages from a non-woven thermal plastic fibrous sheet material. The sheet material is compressed in selected portions to reduce thickness and porosity and to limit an absorbent pad having a greater thickness. The resulting sheet material has a plurality of juxtaposed integral absorbent band packages which can be cut off to contain individual bandages. The thermoplastic fibers are noted as being made of any thermal plastic polymeric material which provides differential melting points. During compressing, thickness of the mat is substantially reduced in selected areas in order to reduce porosity and it is noted that the porosity can be totally eliminated. The porosity is reduced in the areas abutting the absorbent pad area so as to limit the spreading of fluids absorbed in the pad section and confine the fluids to that portion. In the course of the compression, the fibers are bonded together due to the thermoplasticity of the fibers by the application of heat and pressure. The fibers can also be bonded and integrated together by the application of a solvent for the fiber polymer prior to the application of pressure.

A burn healing study published in 1962 by Chardack et al. was initiated with the knowledge that pores of an open cell sponge of formalinized polyvinyl alcohol when embedded in living tissues are rapidly permeated by granulation tissue. The clinical experiences of Chardack et al. supported the previous conclusions that an open cell (formalinized)[1] polyvinyl alcohol sponge becomes and remains adherent to a denuded body surface, whether the latter has resulted from the excision of integument in clean planes or whether it has been filled in by granulation tissue. The adherence of the sponge is predicated upon proliferation of viable granulation tissue into the pores of the sponge. Adherence was confirmed at the first time check point 24 hours after placement. The material can be repeatedly washed, cleansed and ultimately be replaced by autografts. The Ivalon sponge was being used as a surface for tissue ingrowth in burn victims and the open pores were to be in contact with the tissue. The compressed sponge surface was not identified for prevention of tissue ingrowth or reduced tissue shear upon removal of a treated nasal packing. *Synthetic Substitutes For Skin, Chardack et al. Plastic & Reconstructive Surgery*, Vol. 30, No. 5 (November 1962).

[1] added for edification

SUMMARY OF THE INVENTION

The present invention involves a method of manufacture and the resultant product, namely, a fused surface cellular polyvinyl acetal sponge having an untreated body with a pore size ranging generally from about 0.02 to about 1.2 mm, and an absorptive capacity of up to 25 times its own weight in fluid, and a retained holding capacity of 16 times its own weight in fluid as per ASTM D-1117-80 with the treated surface having a substantially closed surface and a reduced pore size from that of the untreated body to reduce or preclude tissue ingrowth.

It is an object of the invention to treat selected surfaces of polyvinyl acetal packing devices for use with nasal, sinus, otic, anal and vaginal cavities to minimize tissue ingrowth into the sponge while leaving other surfaces of the sponge untreated to allow maximum absorption, and wicking of exudate and fluids.

It is another object of the invention to treat selected surfaces of polyvinyl acetal packing devices or other sponge products such that fluid is wicked in, but can not desorb, drip, or leach from the sponge through the treated surfaces.

It is another object of the invention to treat selected surfaces of polyvinyl acetal dressings and other sponge products to form a surface layer which is impermeable to fluids.

It is still another object of the invention to treat the surface of a sponge product to form a surface layer which reduces tissue ingrowth and lessens frictional and shear force required to remove the sponge product from adjacent tissues.

In the accompanying drawings, there is shown an illustrative embodiment of the invention from which these and other of objectives, novel features and advantages will be readily apparent.

DETAILED DESCRIPTION OF THE INVENTION

Figure 1:
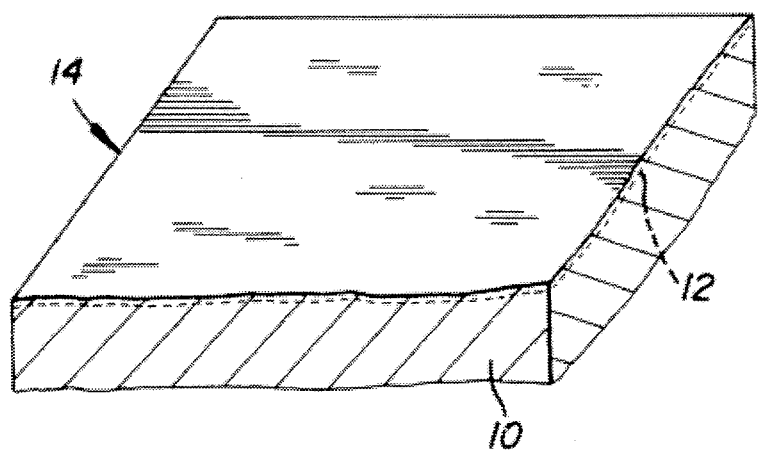
FIG. 1 shows a perspective view of a rectangular wound dressing invention having a fused surface.
Figure 4:
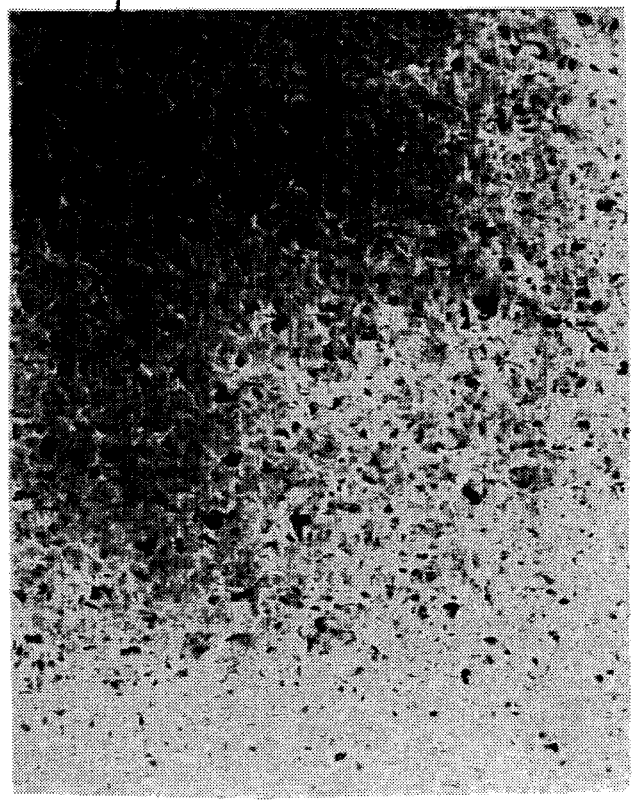
FIG. 4 is a scanning election microscope photograph of the fused surface of the slightly compressed material as set forth in Example 1 at 10×.

The preferred embodiment and best mode of the invention is shown in FIGS. 1 and 4. The foam or sponge products of the invention have been fabricated using commercially produced sponge products sold by Merocel Corporation under the grade designations CF50, CF100, CF150 and CF400. These grade designations have respective average pore diameters of 0.95 mm, 0.45 mm, 0.35 mm and 0.2 mm and an overall range of pore diameter of 0.004–1.2 mm.

Such sponge products (having uniform bulk properties) are exposed to a combination of temperature, pressure, time and other process variables such that the exposed or treated foam surface properties are changed relative to the base or bulk foam to present unique material composites. This process of manufacture has been named for the purposes of this application as "surface fusion".

The altered surface morphology and properties of the present inventive sponge are obtained by fu sing, coating, or metal deposition of the surface of an absorbent sponge. Such treatment is advantageous for sponge dressing device removal when the device is adjacent to tissues (within a body cavity, but not actually surgically attached). Frictional and shear forces required by the physician and experienced by the patient (discomfort, pain) to remove the device are lessened in the case of a substantially closed, relatively non-porous interface. The coefficient of friction is not only lower in the treated surface, but there is minimal opportunity for a three dimensional or geometric interlock relative to the direction of device movement required for removal past dried blood clots or desiccated mucous. This also holds true for sponge dressing removal wherein attachment of the device to the adjacent tissues or tissues is reduced.

Possible attachment mechanisms to dressings include adhesions ("a fibrous band or structure by which bodily parts abnormally adhere"), synechiae ("adhesion of body or tissue parts"), and actual tissue ingrowth ("an inward growth of the adjacent tissue"). Use of the inventive sponge device also provides three dimensional stability when increased structure or support is desired.

Such surface treatment includes single component heterogeneous sponges which are thermally fused or chemically fused as more thoroughly discussed in the following paragraphs.

Surface fusion affects foam density, porosity, texture, absorption, wicking, and/or microstructure at the site of treatment. The type and site(s) of treatment are chosen based upon the intended product application. A foam or sponge product composed of a melt-processable material can be surface treated by exposing it to one or more heated platens, mandrels, etc. under a specified pressure and for a specified time (inert gases may be employed) in the shaping of the sponge product such that differential surface properties are achieved.

Control of the fused surface properties of the present invention is achieved by controlling the process input variables of:

1. Temperature
2. Pressure—constant or variable
3. Exposure time
4. Foam bulk properties
5. Percent compression of foam Surface fusion results in the controlled compaction and fusion of a portion of the homogenous bulk sponge material 10 into a thinner surface layer 12 of increased density. This increased density can then be correlated with a decrease in porosity, absorption, and wicking rate. Surface texture and topography is controlled by design of the heated platen(s), mandrel(s), etc. and surface microstructure is determined by pressure and temperature or by solvent and time exposure.

Advantages available with fused surface technology are:

1. Allows customization of foam and sponge products to specific applications;
2. Reduces the number of materials required (importance notably in medical surgical applications where biocompatability of each material used is important);
3. Increases the bond strength when using adhesives with the treated surfaces (material mating surface is increased and even tailored);
4. Eliminate bonding and adhesion requirements for securing two different materials to form a composite;
5. Create a barrier to microbes, contaminates, etc.; and
6. Impart a three dimensional structure via three dimensional topography such as grooves, corregations etc. by platens, rollers, etc.

There is a present need for surface treated wound dressings, bandages and medical devices. The present medical device is made of a polyvinyl acetal sponge material described in U.S. Pat. No. 4,098,728 issued Jul. 4, 1978. The medical device or dressing 14 is dry, packaged sterile and cut to size. The dressing can also be premoistened with saline or water in a sterile peel pouch.

Figure 2:
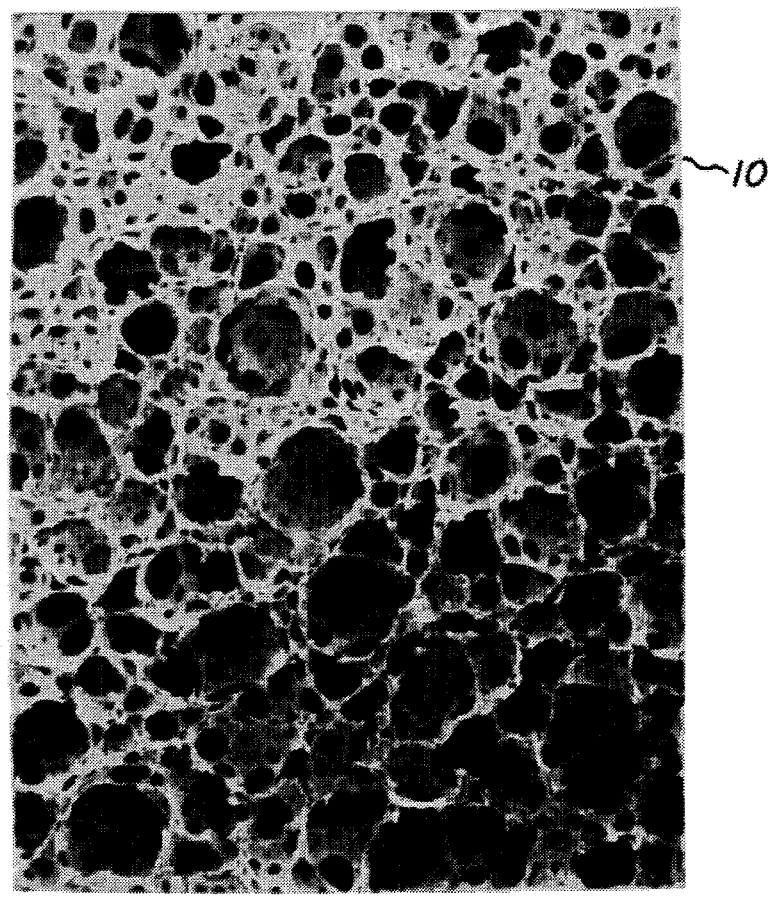
FIG. 2 is a scanning electron microscope photograph of the untreated surface of the polyvinyl acetal material at 10×.

A material used is 15 mm thick Merocel CF50 polyvinyl acetal sponge material, a commercially available material manufactured by the Merocel Corporation. The material is a homogeneous white, open-celled sponge with visible pores, instantaneous fluid wicking, absorptive capacity of up 25 times it weight in fluids, a retained fluid capacity of 16 times its own weight in fluids as measured by ASTM D-1117-80, and a pore size range (diameter) of 0.02 to 1.2 mm as determined by Scanning Electron Microscopy at 10× magnification. The sponge material as seen in FIG. 2 appears as interconnected thin walled structures with holes of circular or oval cross-section and can be hydrated to form a soft device. The device material was treated with approximately 800 psi of pressure at 125° to 150° C. for 3 to 4 seconds. The pressure, time and temperature ranges noted above produced a fused layer in the material ranging from 0.20–0.30 mm in thickness. It was found that fusing the material at 115° C. did not provide a fused surface regardless of the pressure applied or the time period of application. Significant increases in any process variable on the material beyond either 200° C. for 10 seconds with approximately 800 psi of pressure or 180° C. for 30 seconds with approximately 800 psi of pressure will cause degradation.

The fused film layer generally ranges between 0.20–0.30 mm in thickness and can be controlled by varying the process input variables. In this regard the fused surface can have a thickness up to ½ the thickness of the body. Fabrication of the substantially closed surface while maintaining porosity allows exchange of gases including moisture vapor and oxygen through the porous structure of the dressing. The fused surface allows ease of removal of the inventive dressing and precludes tissue ingrowth. Adherence of a dressing or device to viable tissue can cause damage to healing tissue through injury to small blood vessels and regenerating cells.

Manufacture of the present invention and the resulting inventive products with fused surfaces is further described in the following examples.

EXAMPLE 1

A 15 mm thick CF50 Merocel sponge material was die cut into 3 inch square strips. Each strip was pressed with a Dennison hydraulic press equipped with a heated platen at approximately 800 psi pressure for 4 seconds at a temperature of 125° C. After pressure heat treatment, the sponge remained open-celled (pore size unchanged) on all surfaces not contacted by hot plate; the sponge surface that was thermally treated appeared substantially closed and nonporous to the eye with a film thickness of about 0.25 mm. The sample thickness after treatment was reduced to about 14 mm showing a partial and permanent compression of about 8 percent. The treated or fused surface continued to exhibit instantaneous wicking. The absorptive capacity was reduced by about 5 percent from that of the base material (expected due to intentional collapse of about 1/15 of the sponge thickness). A pore size range of 0.01 to 0.45 mm (See FIG. 4) of the fused surface was determined by Scanning Electron Microscopy at 10× which also verified that the number of pores is greatly reduced. The entire sponge remains compressible when dry, expandable when hydrated and soft when wet.

EXAMPLE 2

Figure 3:
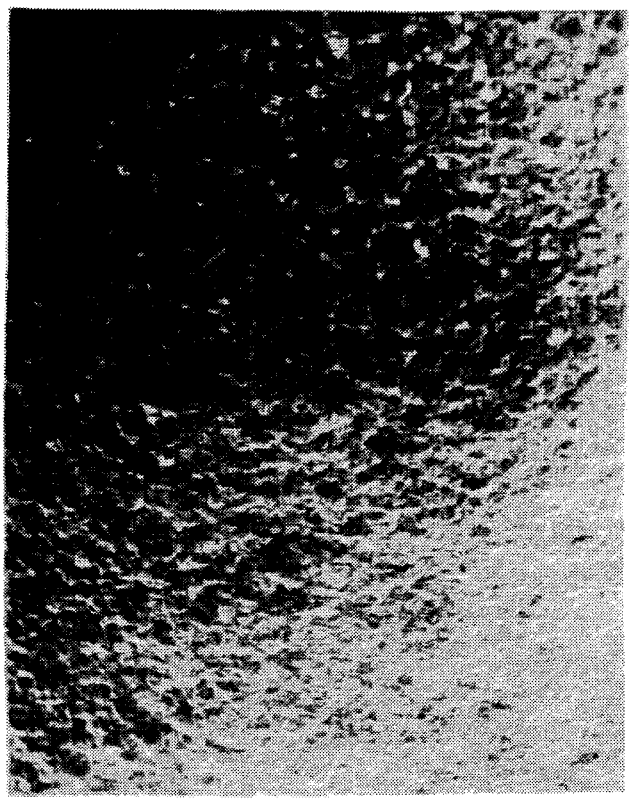
FIG. 3 is a scanning electron microscope photograph of the fused surface of a compressed material as set forth in Example 2 at 10×.

A 15 mm thick CF50 Merocel sponge material was die cut into 3 inch square strips and compressed to 2–3 mm thickness by pressure. Each strip was pressed with a Dennison hydraulic press equipped with a hot plate at approximately 800 psi pressure for 3 seconds at a temperature of 150° C. After treatment, the sponge remained open celled (pore size unchanged) on all surfaces not contacted by hot plate; the sponge surface that was thermally treated appears fully fused, closed and nonporous to the eye with a film thickness of about 0.25 mm. The sample thickness after treatment is about 14 mm. The treated fused surface did not exhibit instantaneous wicking as a water droplet remained on the treated surface for one minute but was absorbed into the sponge body within a period of five minutes. This absorption was primarily attributed to diffusion. The absorptive capacity was reduced by about 5 percent. The surface appeared closed at Scanning Electron Microscopy at 10× (See FIG. 3). The entire sponge remains compressible when dry, expandable when hydrated and soft when wet.

In an alternate embodiment of the invention, the material was chemically fused by acid.

EXAMPLE 3

A dry and compressed 15 mm thick CF50 Merocel sponge material was brought into contact with dichloroacetic acid puddled on a flat surface for a period of between 3 to 7 seconds until the acid wetted the sponge. After approximately 1 minute, the entire sponge was immersed in copious amounts of water for 5 minutes and then thoroughly washed and rinsed in water to remove the dichloroacetic acid. The surface of the sponge which engaged the acid appeared substantially closed; the sponge thickness was reduced to 12–14 mm. The treated sponge was shown to absorb water instantaneously through the treated surface. The bulk properties of the base material, including wet strength of the material appeared unchanged and the treated surface layer could not be delaminated from the bulk sponge.

The treated sample was allowed to dry overnight. A water droplet at room temperature was placed on the treated surface and absorption of the water through the treated surface was seen at approximately one minute. This was compared to untreated MEROCEL sponge which absorbs water instantaneously.

The same result was obtained by brushing a thin layer of the dichloroacetic acid on to a sponge sample of the same material and washing the sponge sample as previously noted.

It is also envisioned that alcohols, and/or solvents could be used on the Merocel material surface. As an example the solvent Dimethyl sulfoxide placed on the sponge surface by controlled vapor-phase exposure for an established time period has been found to alter the sponge surface. Liquid-phase solvent exposure can be employed in numerous ways including direct contact, brushing, and spraying with standard pressure nozzles or ultrasonic nozzles.

Another embodiment of the invention utilizes sponge coatings. In this embodiment a Merocel CF50 sponge was coated with room temperature vulcanizing (RTV) Silicone as shown by the following example.

EXAMPLE 4

Specimens were cut in 3 inch square strips from CF50 material and weighed about 5.0 g. The fully expanded thickness of the material was 15 mm. The specimens were first weighed and coated with RTV Silicone by a brush or doctor blade. The coating thickness ranged from 0.3 mm to 0.6 mm. The Silicone used was Dow Corning 734 Flowable Sealant. The specimens were allowed to cure overnight and then compared with non-treated CF50.

The absorptive capacity of the specimens was reduced approximately 29%. Wicking of water was instantaneous through untreated surfaces. The treated surface does not absorb water indicating sealing of the sponge pores.

It is also envisioned that metal deposition including noble metals such as gold, platinum, silver, and palladium or base metals such as aluminum, copper and zinc could be applied to the surface of the sponge material. A chemical deposition such as polytetrafluoroethylene (PTFE), hydrogels, fatty glycerol esters could also be used on the surface of the sponge material.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A surgical sponge device comprising;
   a sterile surgical device body constructed of an open cell polyvinyl acetal foam material having a pore diameter size which is not greater than 1.2 mm and instantaneous wicking properties, at least one surface of said body being treated to form a layer with reduced porosity with the pore diameters of the layer ranging from 0.01 to 0.45 mm and a thickness which is less than ½ the thickness of the device body, a controlled absorbency and a substantially closed outer surface reducing tissue ingrowth and device removal shear forces.

2. A sponge device as claimed in claim 1 wherein said sterile sponge device surface layer has a thickness ranging from 0.20 to 0.30 mm in thickness.

3. A sponge device as claimed in claim 1 wherein said sterile sponge device surface layer has a thickness ranging from 0.30 to 0.60 mm in thickness.

4. A sponge device as claimed in claim 1 wherein said sterile sponge device film layer is about 0.25 mm in thickness.

5. A sponge device as claimed in claim 1 wherein said sterile sponge device body has a porosity ranging from 0.004 to 1.2 mm.

6. A sponge device as claimed in claim 1 wherein said sterile sponge device body has an average pore diameter ranging from 0.2 to 0.95 mm.

7. A unitary surgical sponge device characterized by the ability to absorb body fluid while precluding tissue ingrowth comprising;

a sterile surgical device body constructed of a polyvinyl acetal having a pore diameter size generally ranging from 0.02 mm to 1.2 mm and instantaneous fluid wicking, at least one surface of said body being fused to form a film layer having reduced porosity from the device body with the pore diameters of the layer ranging from 0.01 to 0.45 mm to form a substantially closed surface and reduce tissue ingrowth, said film layer having a time of absorbency to absorb fluid within the device body from instantaneous to 5 minutes.

8. A wound dressing device characterized by the ability to absorb body fluid while precluding tissue ingrowth comprising;

a sterile surgical device body constructed of a rectangular body about ¼ inch in thickness composed of a premoistened polyvinyl acetal material having a pore diameter size generally ranging from 0.02 mm to 1.2 mm and instantaneous wicking, at least one surface of said body being fused to form a film layer about 0.25 mm in thickness having reduced porosity from the device body with an average pore diameter of about 0.02 mm to form a substantially closed smooth surface and reduce tissue ingrowth, said film layer having an instantaneous fluid absorbency.

9. A surgical sponge device comprising:

a sterile surgical device body constructed of an open cell foam polyvinyl acetal material having a pore diameter size which is not greater than 1.2 mm and instantaneous wicking, at least one surface of said body being treated to form a closed substantially impervious outer layer having a thickness which is less than ½ the thickness of the device body, reducing tissue ingrowth and device removal shear forces.

10. A sponge device as claimed in claim 9 wherein said sterile sponge device treated surface is an acid chemical reaction product with polyvinyl acetal resulting in said sterile sponge layer having reduced permeability.

11. A nasal pack device characterized by the ability to absorb body fluid while precluding tissue ingrowth comprising;

a sterile surgical device body constructed of a generally rectangular body ranging from 7–15 mm in thickness of polyvinyl acetal having a pore diameter size generally ranging from 0.02 mm to 1.2 mm and instantaneous wicking, at least one surface of said body being fused to form a film layer ranging from about 0.20–0.30 mm in thickness having reduced porosity from the device body to form a substantially closed smooth surface and reduce tissue ingrowth, said film layer having an instantaneous fluid absorbency.

12. A nasal pack device as claimed in claim 11 wherein said nasal pack is premoistened.

13. A one piece nasal pack device characterized by the ability to absorb body fluid while precluding tissue ingrowth comprising;

a sterile surgical device body constructed of a generally rectangular body ranging from 7–15 mm in thickness composed of polyvinyl acetal having a pore diameter size generally ranging from 0.02 mm to 1.2 mm, at least one surface of said body being fused to form a substantially closed film layer about 0.25 mm in thickness with a smooth outer layer to reduce tissue ingrowth.

14. A surgical sponge device comprising;

a sterile surgical device body constructed of an open cell polyvinyl acetal foam material having a pore diameter size which is not greater than 1.2 mm and instantaneous wicking properties, at least one surface of said body being treated with silicone to form a silicone coated layer with reduced porosity, a thickness which is less than ½ the thickness of the device body, a controlled absorbency and a substantially closed outer surface reducing tissue ingrowth and device removal shear forces.

* * * * *